United States Patent [19]

Pearce

[11] 4,430,269
[45] Feb. 7, 1984

[54] 12'-IODO DERIVATIVES OF DIMERIC INDOLE-DIHYDROINDOLE ALKALOIDS, AND PROCESS FOR PREPARING THEM

[75] Inventor: Homer L. Pearce, Indianapolis, Ind.

[73] Assignee: Eli Lilly and Company, Indianapolis, Ind.

[21] Appl. No.: 364,384

[22] Filed: Apr. 1, 1982

[51] Int. Cl.³ .................. C07D 519/04; C07D 471/22
[52] U.S. Cl. ................................................. 260/244.4
[58] Field of Search ........................... 260/244.4, 243.3

[56] References Cited

U.S. PATENT DOCUMENTS 3,574,220  4/1971  Sallay .............................. 260/244.4 X
4,307,100  12/1981  Langlois et al. ..................... 424/262

FOREIGN PATENT DOCUMENTS 924041  4/1963  United Kingdom ............. 260/244.4

*Primary Examiner*—Donald G. Daus
*Assistant Examiner*—Diana G. Rivers
*Attorney, Agent, or Firm*—James L. Rowe; Arthur R. Whale

[57] ABSTRACT

12'-Iodo VLB, and related 5-iodo-2,3-disubstituted indoles; and a method for their preparation.

6 Claims, No Drawings

12'-IODO DERIVATIVES OF DIMERIC INDOLE-DIHYDROINDOLE ALKALOIDS, AND PROCESS FOR PREPARING THEM

BACKGROUND OF THE INVENTION

The alkaloids obtainable from *Vinca rosea* represent one of the most productive areas of chemistry for drugs which adversely affect the growth of experimental malignancies in mammals. Initially, only some of the alkaloids, obtainable from the leaves of the plant by extraction and purifiable by chromatography, were found to be active. These active antineoplastic alkaloids obtained directly from the leaves of the vinca plant were all found to have a dimeric indole-dihydroindole structure:

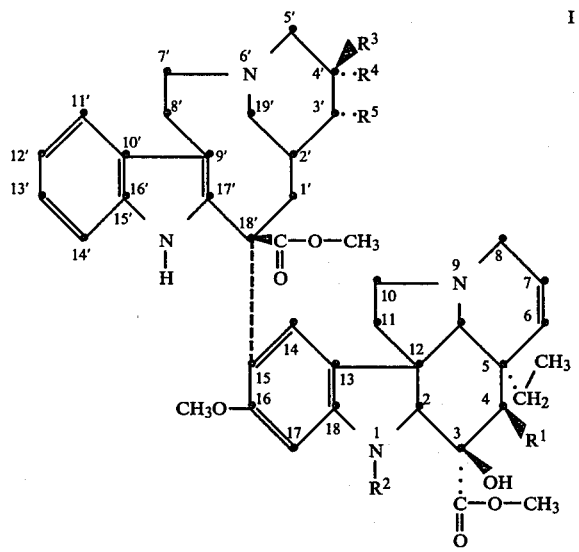

In the above formula, where $R^1$ is acetoxy, $R^2$ is methyl, $R^3$ is hydroxyl, $R^4$ is ethyl and $R^5$ is H, VLB (vincaleucoblastine, vinblastine) is represented; where $R^1$ is acetoxy, $R^2$ is formyl, $R^3$ is hydroxyl, $R^4$ is ethyl and $R^5$ is H, vincristine is represented; where $R^1$ is acetoxy, $R^2$ is methyl, $R^3$ is ethyl, $R^4$ is hydroxyl, and $R^5$ is H, leurosidine is represented; where $R^1$ is acetoxy, $R^2$ is methyl or formyl, $R^3$ is ethyl and $R^4$ and $R^5$ taken together with the carbons to which they are attached form an α-epoxide ring, leurosine and leuroformine, respectively are represented; where $R^1$ is acetoxy, $R^2$ is methyl, $R^3$ is ethyl, and $R^4$ and $R^5$ are H, deoxy VLB "B" or 4'-deoxyleurosidine is represented; where $R^1$ is acetoxy, $R^2$ is methyl, $R^4$ is ethyl and $R^3$ and $R^5$ are H, deoxy VLB "A" or 4'-deoxy VLB is represented; where $R^1$ is H, $R^3$ and $R^5$ are OH, $R^4$ is ethyl and $R^2$ is $CH_3$, 4-desacetoxy-3'-hydroxy VLB is represented; where $R^1$ and $R^5$ are H, $R^3$ is OH, $R^4$ is ethyl and $R^2$ is methyl, 4-desacetoxy VLB is represented; and where $R^1$ is acetoxy $R^3$ and $R^5$ are OH, $R^4$ is ethyl and $R^2$ is methyl, vincadioline is represented.

Literature references to the above alkaloids are as follows: leurosine (U.S. Pat. No. 3,370,057), VLB (U.S. Pat. Nos. 3,097,137, and 4,305,875), leuroformine (Belgian Patent No. 811,110), leurosidine (vinrosidine) and leurocristine (to be referred to hereafter as vincristine) (both in U.S. Pat. No. 3,205,220), vincadioline (U.S. Pat. No. 3,887,565), 4-desacetoxy VLB (U.S. Pat. No. 3,954,773), and 4-desacetoxy-3'-hydroxy VLB (U.S. Pat. No. 3,944,554).

Two of the above alkaloids, VLB and vincristine, are now marketed for the treatment of malignancies, particularly the leukemias and related diseases, in humans. The two marketed alkaloids are customarily administered by the i.v. route. Two others, leurosidine and leuroformine, have been on clinical trial in the U.S. or in Europe.

Chemical modification of the Vinca alkaloids started slowly for several reasons. In the first place, the molecular structures involved are extremely complex, and chemical reactions which modify one specific functional group of the molecule without affecting other groups have been difficult to develop. Secondly, dimeric alkaloids lacking desirable chemotherapeutic properties have been recovered or produced from *Vinca rosea* extracts, and a determination of their structures has led to the conclusion that these inactive compounds are closely related structurally to, and even isomeric with, one or more of the active alkaloids.

One of the more recent, and more successful, modifications of the basic indole-dihydroindole structure has been the preparation of C-3 carboxamide and carboxhydrazide derivatives. Many of these are highly active anti-tumor agents (see U.S. Pat. 4,166,810, and Conrad et al. *J. Med. Chem.*, 22, 391 (1979). 4-Desacetyl VLB 3-carboxamide (vindesine) is currently being marketed in several European countries as an oncolytic agent. It is said to be effective in treating some vincristine-resistant leukemias.

Most of the chemical modifications of the dimeric indole-dihydroindole alkaloids have involved modifying a functionality already present in the molecule; i.e., ester to amide at C-3, changing C-4 ester group, formyl for methyl at N-1, dehydration at C-4' and adjacent carbons, converting C-3 hydroxy and ester to spiro-oxazolidinedione, changing 3',4'-epoxide to 3'-hydroxy etc. Direct substitution of new chemical groups or atoms into the complex ring structure has been rare; see, for example, preparation by Barnet et al. (U.S. Pat. No. 4,110,330) of a 5'-acetonyl VLB derivative where the acetonyl group ($CH_3$—CO—$CH_2$) replaces one of the C-5' hydrogens.

Aromatic substitution in the vindoline (dihydroindole) moiety is known and the substituent usually enters the ring at C-17, ortho to both the methoxy and dialkylamine groups—see for example Teale et al., *Brit. J. Pharm.*, 4, 169(1977) who also prepared C-9' derivatives. Substitution in the phenyl moiety of the upper indole (catharanthine) portion of the molecule is not known, probably because aromatic substitution is favored at C-17 in the lower portion for the reasons set forth above.

A combination of iodine and periodic acid in acetic acid have been used to iodinate polyalkylbenzenes containing bulky groups—see *Bull. Chem. Soc.* (Japan), 39, 129 (1956).

It is an object of this invention to provide 12'-iodo substituted dimeric indole-dihydroindoles.

SUMMARY OF THE INVENTION

In fulfillment of the above and other objects, this invention provides compounds of the formula:

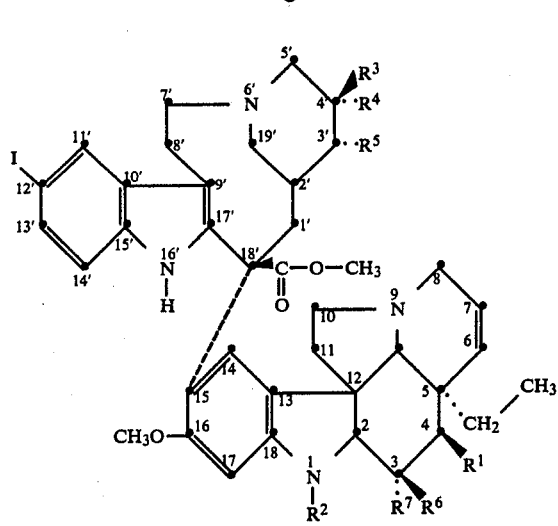

wherein $R^1$ is H, OH, O—CO—CH$_3$, or O—CO—CH$_2$R$^8$, wherein $R^8$ is Cl, morpholino, dimethylamino, cyclopropylmethylamino and methylamino, $R^2$ is H, CH$_3$ or CHO; when $R^3$ and $R^5$ are taken singly, $R^5$ is H or OH, one of $R^3$ and $R^4$ is ethyl and the other is H or OH; when $R^3$ and $R^5$ are taken together with the carbons to which they are attached, they form an oxirane ring or a vinyl group, in either of which cases, $R^4$ is ethyl; when taken singly, $R^6$ is OH and $R^7$ is CO—OCH$_3$ or CO—R$^9$, wherein $R^9$ is NH$_2$, NH$_2$—NH$_2$, NH—C$_{1-3}$ alkyl, NH-substituted C$_{1-3}$alkyl (wherein said substituents can be one or two members of the group chloro and bromo), or C$_{1-3}$ loweralkanoyloxy; when $R^6$ and $R^7$ are taken together with the carbon atoms to which they are attached, they form a spiro-oxazolidinedione ring permissibly substituted at N$_3''$ with C$_{1-3}$ alkyl or chloro-substituted C$_{1-3}$alkyl; and pharmaceutically acceptable acid addition salts thereof formed with relatively non-toxic acids.

The compounds of this invention (formula II above) are prepared by reacting a compound according to formula II lacking an iodine at C-12' with an iodinating mixture containing a ferrous salt such as the perchlorate or sulfate salt, a periodate, preferably one soluble in organic solvents such as tetrapropylammonium periodate, ruthenium dioxide and glacial acetic acid in acetonitrile or other suitable inert solvent. The 12'-iodo derivative thus prepared is isolated and purified by standard procedures. Yields of the desired product are in the range 85-95%.

In addition to direct iodination of compounds according to formula II lacking the 12'-iodine, it is possible to prepare certain compounds coming within the scope of this invention from other compounds already carrying a 12'-iodo group. For example, 12'-iodovincristine, 12'-iodo-4'-deoxy-1-desmethyl-1-formylleurosidine and 12'-iodoleuroformine can be prepared from 12'-iodo VLB, 12'-iodo-4'-deoxyleurosidine and 12'-iodoleurosine by low temperature (−80° C.) chromic acid oxidation. (See, for example, the processes or U.S. Pat. Nos. 4,143,041, 3,899,493 and 4,189,432). 12'-iodovindesine can be prepared from 12'-iodo VLB by forming 12'-iodo-4-desacetyl VLB carboxhydrazide, converting the carboxhydrazide to the corresponding carboxazide and then reacting the carboxazide with ammonia, according to the procedure of U.S. Pat. No. 4,203,898—see also Conrad et al., J. Med. Chem., 22, 391 (1979). Other 12'-iodo-4-desacetyl VLB carboxamides can be prepared in similar fashion from the 3-carboxazide plus the requisite amine, as can C-3 carboxamides of other vinca alkaloids represented by I above—see also U.S. Pat. No. 4,203,898.

The preparation of the 12'-iodo-4-desacetyl VLB 3-(2-chloroethyl)amide is not disclosed therein but can be prepared either by direct iodination of 4-desacetyl VLB 3-(2-chloroethyl)amide or by converting 12'-iodo VLB to 12'-iodo-4-desacetyl VLB 3-hydrazide, then to 12'-iodo-4-desacetyl VLB 3-azide. The azide is reacted, according to standard procedures, with 2-chloroethylamine to yield the desired 12'-iodo-4-desacetyl VLB 3-(2-chloroethyl)amide. Alternatively, 4-desacetyl VLB 3-(2-hydroxyethyl)amide can be converted to the 2-chloroethylamide with triphenylphosphine and CCl$_4$ and the 2-chloroethylamide thus prepared iodinated by the procedure of this invention to yield the desired 12'-iodo compound.

Alternatively, a 3-ester or 3-carboxamide according to II above can be converted to a 3-spiro-5''-oxazolidine-2'',4''-dione by the procedure of U.S. Pat. No. Re. 30,560. For example, treatment of 4-desacetyl VLB 3-carboxamide with 2-chloroethylisocyanate produces a spiro-oxazolidinedione which, after iodination by the process of this invention, yields 12'-iodo-4-desacetyl VLB 3''-(2-chloroethyl)-3-spiro-5''-oxazolidine-2'',4''-dione. The same compound can be produced by reaction of 12'-iodo VLB with 2-chloroethylisocyanate. This compound, after treatment with aqueous alkali, yields the corresponding 4-desacetyl derivative. Hydrolysis of the oxazolidinediones thus produced yields, respectively, 12'-iodo VLB 3-(2-chloroethyl)amide and 12'-iodo-4-desacetyl VLB 3-(2-chloroethyl)amide. Other 3''-substituted oxazolidine-2'',4''-diones where the 3''-substituent is C$_{1-3}$ alkyl or chloro-substituted C$_{1-3}$ alkyl are prepared in similar fashion by using the appropriate isocyanate in its reaction with a 12'-iodo-C-3 ester or amide.

By an analogous series of reactions, leurosine can be treated with Raney nickel by the process of Neuss et al., Tetrahedron Letters, 811 (1967) to produce a mixture of 4'-deoxyleuorsidine and, in smaller amounts, 4'-deoxy VLB. 4'-Deoxy leurosidine and 4'-deoxy VLB, after separation and purification, can individually be iodinated to yield the corresponding 12'-iodo derivatives. Each of these iodo derivatives can in turn be oxidized with chromate or chromic oxide at low temperatures to form the two corresponding 12'-iodo vincristine or 12'-iodo-1-formylleurosidine.

The 12'-iodo-4-desacetyl derivatives can be transformed to the corresponding 4-chloroacetyl derivatives by the process set forth in U.S. Pat. No. 3,392,173. Conversion of the 4-chloroacetyl derivative to a 4-dialkylaminoacetyl derivative is disclosed in U.S. Pat. No. 3,387,001.

In another series of reactions, VLB, vincristine and other 4'-hydroxy vinca dimers can be dehydrated to yield a mixture of three anhydro derivatives, one of which is 3',4'-anhydro-4-desacetyl VLB, 3,4'-anhydro-4-desacetyl vincristine, etc. The corresponding 4-acetyl anhydro VLB compounds (called also Δ$^{20}$-dehydroxy-20' VLB) are available by the process of U.S. Pat. No. 4,305,875. These anhydro derivatives can be duly transformed to the corresponding 12'-iodo derivatives by the process of this invention.

Any of the 4-desacetyl derivatives prepared as indicated above can be reacetylated by the procedure of U.S. Pat. No. 3,392,173.

Thus, it can be seen that, starting with 12'-iodo-VLB or similar compounds coming within the scope of formula II in which one of $R^3$ or $R^4$ is hydroxy and $R^2$ is methyl or with leurosine ($R^3$ and $R^5$ form an oxygen bond and $R^2$ is methyl), all of the other derivatives coming within the scope of formula II can be prepared. Iodination at C-12' can in general be accomplished initially with a given starting material (subject to certain exceptions as will be apparent to those skilled in the art) and the 12'-iodo derivative carried through to the final product. Alternatively, an intermediate or final product can be iodinated (Formula II lacking the 12'-iodo group). There are thus a multitude of pathways which can be utilized to prepare the compounds of this invention. Those skilled in the art will also recognize that the possibility of a side reaction between the 12'-iodo and a reagent used to prepare the particular derivative can be avoided by carrying out the iodination after all other reactions used in forming the particular vinca dimer derivative have already been completed.

The oxidative iodination reagent which I employ in my novel process consists of a ferrous salt, ruthenium dioxide, a periodate and an organic acid. A mutual, polar organic solvent is employed. The function of the organic acid is to solubilize the free base of the dimeric indole-dihydroindole alkaloid or derivative thereof and also to protect N-8 and N-6' from oxidative attack thereon (formula II except that C-12' carries H, not I). However, an acid addition salt of the base can be used provided the particular salt has the requisite solubility in the mutual organic solvent employed. The ferrous salt should also be soluble in the polar organic solvent. Ferrous perchlorate has been successfully employed when acetonitrile is the organic solvent of choice. In general, I prefer to use a periodate which is soluble in polar organic solvents. The tetraalkylammonium salts of periodic acid have such solubility and therefore form a particularly useful type of periodate for use in my novel process. However, such periodates as sodium periodate have sufficient solubility in the reaction mixture to permit the iodination reaction to proceed. Ruthenium dioxide is customarily employed as a pentahydrate, although other crystal forms are fully operative. Acetonitrile has been specified above, and it is the solvent of choice. However, other solvents such as dimethylformamide, ethyl acetate and 1,2-dimethoxyethane can be used. The reaction is conveniently carried out at a temperature in the range $-30°$ C. to $0°$ C.

The following example illustrates this invention.

EXAMPLE 1

Preparation of 12'-iodo VLB

A solution of 419 mg. of VLB free base dissolved in 1.5 ml. of acetonitrile (distilled and degassed with nitrogen) was prepared. 0.75 ml. of glacial acetic acid were added. This solution was in turn added to a stirred mixture containing 1.13 g. of ferrous perchlorate in 3 ml. of specially purified acetonitrile at about $-20°$ C. Twelve milligrams of ruthenium dioxide pentahydrate were added to the cold solution followed by a solution containing 390 mg. of tetra-n-propylammonium periodate in 2 ml. of acetonitrile. The consequent reaction mixture was allowed to stir at $-20°$ C. The course of the reaction was monitored by TLC and HPLC analysis of aliquots. After 26 hours, these analyses indicated that the degree of conversion to the desired 12'-iodo derivative was 46%. At this time, an additional 390 mg. of tetra-n-propylammonium periodate was added and the reaction stirred for additional 4 hours at which time the reaction was shown to be virtually complete by HPLC. The reaction mixture was then extracted with methylenedichloride and the methylenedichloride layer was washed with 1 N aqueous sodium sulfite and 14 N aqueous ammonium hydroxide. The methylenedichloride layer was separated and dired. Evaporation of the methylenedichloride left 12'-iodo VLB as a residue. HPLC was carried out on the residue in a 30 cm. $\times 0.4$ cm. column with a $C_{18}$ Reverse Phase support with a mixture of 75% methanol and 25% water containing 0.2 ml. of triethylamine per liter as the eluant—flow rate=1.25 ml. per minute.

The above reaction was repeated with the following quantities. 2.75 g. of ferrous perchlorate in 5 ml. of acetonitrile were stirred and cooled to $-20°$ under a nitrogen atmosphere. 1.023 g. of VLB free base in 5 ml. of acetonitrile were added plus 1.89 ml. of glacial acetic acid. 281 mg. of ruthenium dioxide pentahydrate were added to this mixture followed by 1.07 g. of tetra-n-propylammonium periodate over a 35 minute period. 100 $\mu$l. of water were then added and the resulting mixture stirred at $-20°$ C. overnight. No reaction had occurred according to HPLC. 2.37 g. of tetra-n-propylammonium periodate were then added in one portion. The reaction mixture was stirred for two hours at $-20°$ C. at which time HPLC analysis indicated that there had been a 55% conversion to 12'-iodo VLB. After 40 hours, HPLC indicated that there had been an 87% conversion.

The total reaction mixture was poured into 350 ml. of methylenedichloride with stirring. The resulting mixture was filtered through glass wool and the filtrate washed successively with 100 ml. portions of 50% 14 N aqueous ammonium hydroxide, 50% saturated aqueous sodium bicarbonate and 1 N aqueous sodium sulfite. The organic layer was separated, dried and then concentrated to yield 1.91 g. of a crude product. A 300 ml. reverse phase C18 silica column (20 micron particle size) was used to purify the residue. The eluant consisting of 75% methanol, 25% water with 0.2 ml. of triethylamine per liter. The column was run at a rate of 12 ml. per minute. Fifteen ml. fractions were obtained. 12'-iodo VLB was found in fractions 35–50. These fractions, containing the desired product, were combined and the solvent evaporated therefrom. 0.51 g. (43% yield) of 12'-iodo VLB free base were obtained.

The free base was converted to the sulfate salt by adding 2.81 ml. of 2% sulfuric acid in anhydrous ethanol to a solution of 0.51 g. of 12'-iodo VLB in 20 ml. of anhydrous ethanol. The precipitated sulfate salt was isolated by centrifugation and the centrifugate washed with 20 ml. of isopropanol and 20 ml. of ether. 0.57 g. of 12'-iodo VLB sulfate were obtained. Mass spectrum: m/e at 936; nmr was consistent with the 12'-iodo VLB structure.

EXAMPLE 2

Alternate Preparation of 12'-iodo VLB

Two hundred mg. of VLB free base were dissolved in 0.25 ml. of acetonitrile at about $-30°$ C. One hundred seventy $\mu$l. of acetic acid, 537 mg. of ferrous perchlorate and 317 mg. of sodium meta-periodate and 5 $\mu$l. of water were added thereto in that order. The reaction mixture was stirred at about −35° C. overnight. HPLC analysis indicated no reaction had taken place. Five mg. of ruthenium dioxide pentahydrate were then added. The mixture was warmed to about −15° C. and was then stirred at −15° C. overnight. HPLC reverse phase chromatography indicated that a new product (not vincristine) had been prepared. The reaction mixture was then allowed to stir for an additional 6 hours at about 0° C. One ml. of 15% aqueous sodium sulfite and 1 ml. of 14 N aqueous ammonium hydroxide were added to quench the reaction. The resulting mixture was diluted with 75 ml. of methylenedichloride and the methylenedichloride layer separated. The methylenedichloride layer was washed with 10 ml. of water and 10 ml. of saturated aqueous sodium chloride and was then dried. Removal of the solvent in vacuo yielded 204 mg. of a crude product. The crude product was chromatographed over 20 g. of silica packed in methylenedichloride. The chromatogram was developed with 50 ml. portions of methylenedichloride containing 1, 2, 4 and 8% methanol. 12'-iodo VLB was isolated with 8% methanol; yield=16 mg.

The compounds of this invention have activity against transplanted tumors in mice. For example, 12'-iodo VLB sulfate shows anti-neoplastic activity against B16 melanoma, P-1534PJ leukemia, and CA-755 adenocarcoma with intraperitoneal dosages in the range 6.25 to 12.5 mg./kg. administered every third day to the tumor-bearing mice. The compounds of this invention would be employed in the treatment of neoplasms utilizing the same routes of administration as VLB, vincristine and vindesine and against similar tumors but at somewhat higher dose levels.

More importantly, however, the compounds of this invention can be utilized as radiochemical tracers by employing radioactive iodine ($I^{131}$) as part of the iodine content of the periodate reactant. VLB tagged at C-12' with $I^{131}$ can be used to follow the metabolism of VLB, tissue binding, excretion etc. as well as having a potential use in certain radio-immune assays.

In another aspect of this invention, I have found that catharanthine (formula III where X is H)

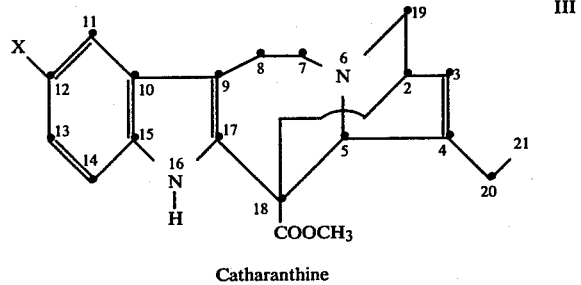

Catharanthine can be iodinated at the C-12 to yield 12-iodocatharanthine (formula III wherein X is I). The procedure is the same as that employed for the iodination of the dimeric dihydroindole alkaloids. An iodination takes place at the same relative carbon atoms, C-12, in the indole monomer. An illustrative example of this process follows.

EXAMPLE 3

Preparation of 12-iodocatharanthine

A solution of 5.55 g. of ferrous perchlorate hexahydrate in 30 ml. of acetonitrile was degassed, flushed with nitrogen and then cooled to about −30° C. A second solution containing 1 g. of catharanthine hydrochloride and 3.64 ml. of glacial acetic acid in 5 ml. of acetonitrile were added to the first solution with stirring while maintaining the temperature at about −30° C. Next, 0.56 g. of ruthenium dioxide pentahydrate was added in one portion followed by 3.519 g. of potassium periodate, also in a single portion. Finally, 100 microliters of water were added. The reaction mixture was stirred at about −30° C. for about 48 hours. The reaction mixture was then diluted with an equal volume of methylenedichloride and the resulting organic layer separated and the separated layer washed twice with 15% aqueous sodium sulfite followed by a dilute ammonium hydroxide wash and an aqueous saturated sodium chloride wash. The organic layer was dried and filtered and the organic solvents removed in vacuo to obtain a crude product; weight=388 mg. The crude product was purified by $C_{18}$ reverse phase HPLC using the same solvent system as in Example 1. 59 mg. of 12-iodocatharanthine were obtained.

12-iodocatharanthine can be coupled with vindoline via a Polonowski fragmentation procedure to yield 12'-iodo-3',4'-anhydro VLB which compound can in turn be converted to 12'-iodoleurosidine or 12'-iodoleurosine. Thus, the 12-iodocatharanthine if iodinated with $I^{131}$ gives a alternate method of preparing tagged dimeric vinca indole-dihydroindole alkaloids, and also makes potentially accessible iodinated (and tagged) derivatives not presently known which can be derived via a Polonowski fragmentation procedure between catharanthine and other monomers than vindoline.

The iodination process of this invention, whereby an iodine atom is introduced into the phenyl ring of an indole para to the indole nitrogen, has been illustrated with regard to two 2,3-disubstituted indoles, VLB and catharanthine, where the substituents on C-2 and C-3 are alkyl or substituted alkyl groups. As will be apparent to those skilled in the art, my novel iodination process is applicable generally to the iodination of 2,3-disubstituted indoles.

I claim:

1. A compound of the formula

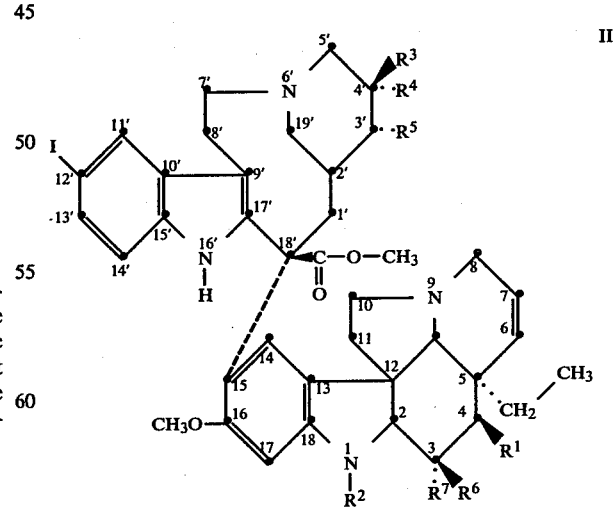

wherein $R^1$ is H, OH, O—CO—CH$_3$, or O—CO—CH$_2$R$^8$, wherein R$^8$ is Cl, morpholino, dimethylamino, cyclopropylmethylamino and methylamino, R$^2$ is H, CH₃ or CHO; when R³ and R⁵ are taken singly, R⁵ is H or OH, one of R³ and R⁴ is ethyl and the other is H or OH; when R³ and R⁵ are taken together with the carbons to which they are attached, they form an oxirane ring or a vinyl group, in either of which cases, R⁴ is ethyl; when taken singly, R⁶ is OH and R⁷ is CO—OCH₃ or CO—R⁹, wherein R⁹ is NH₂, NH₂—NH₂, NH—C₁₋₃ alkyl, NH-substituted-C₁₋₃-alkyl (wherein said substituents can be one or two members of the group chloro and bromo), or C₁₋₃ loweralkanoyloxy; when R⁶ and R⁷ are taken together with the carbon atoms to which they are attached, they represent a spiro-oxazolidinedione ring permissibly substituted at N₃″ with C₁₋₃ alkyl or chloro-substituted C₁₋₃alkyl; and pharmaceutically acceptable acid addition salts thereof formed with relatively non-toxic acids.

2. A compound according to claim 1, said compound being 12′-iodo VLB.

3. 12-iodocatharanthine.

4. The process of preparing a compound according to claim 1 which comprises reacting a compound of the structure.

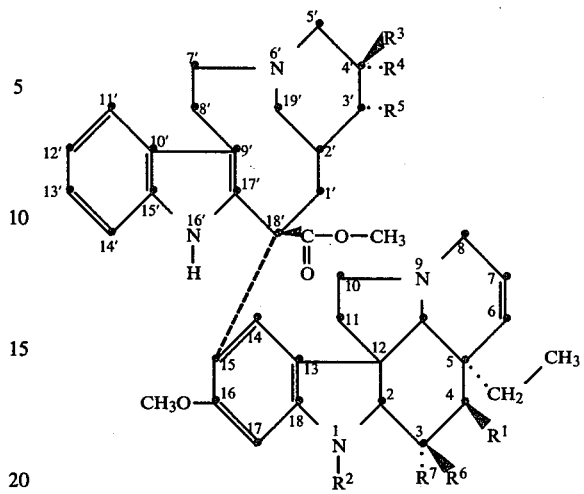

wherein R¹ is H, OH, O—CO—CH₃, or O—CO—CH₂R⁸, wherein R⁸ is Cl, morpholino, dimethylamino, cyclopropylmethylamino and methylamino, R² is H, CH₃ or CHO; when R³ and R⁵ are taken singly, R⁵ is H or OH, one of R³ and R⁴ is ethyl and the other is H or OH; when R³ and R⁵ are taken together with the carbons to which they are attached, they form an oxirane ring or a vinyl group, in either of which cases, R⁴ is ethyl; when taken singly, R⁶ is OH and R⁷ is CO—OCH₃ or CO—R⁹, wherein R⁹ is NH₂, NH₂—NH₂, NH—C₁₋₃ alkyl, NH-substituted-C₁₋₃-alkyl (wherein said substituents can be one or two members of the group chloro and bromo), or C₁₋₃ loweralkanoyloxy; when R⁶ and R⁷ are taken together with the carbon atoms to which they are attached, they represent a spiro-oxazolidinedione ring permissibly substituted at N₃″ with C₁₋₃ alkyl or chloro-substituted C₁₋₃-alkyl, or an acid addition salt thereof, with a reagent containing a soluble ferrous salt, a soluble periodate salt, RuO₂, acetic acid and an inert polar organic solvent.

5. A process according to claim 4 in which the ferrous salt used is ferrous perchlorate.

6. A process according to claim 4 in which acetonitrile is used as the mutual inert polar solvent.

* * * * *